(12) United States Patent
Snell et al.

(10) Patent No.: US 7,338,436 B1
(45) Date of Patent: Mar. 4, 2008

(54) IMPLANTABLE CARDIAC PHYSICAL MOTION MAPPING DEVICE

(75) Inventors: Jeffery D. Snell, Chatsworth, CA (US); Annapurna Karicherla, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 91 days.

(21) Appl. No.: 11/167,989

(22) Filed: Jun. 27, 2005

(51) Int. Cl.
*A61F 2/00* (2006.01)

(52) U.S. Cl. .................. 600/37; 600/16; 600/409; 600/527; 607/6

(58) Field of Classification Search ........... 600/16, 600/17, 37, 409, 513, 527; 607/6, 19
See application file for complete search history.

(56) References Cited

U.S. PATENT DOCUMENTS

| | | | |
|---|---|---|---|
| 5,195,525 A | 3/1993 | Pelc | 128/653.2 |
| 5,358,519 A * | 10/1994 | Grandjean | 623/3.12 |
| 6,099,460 A * | 8/2000 | Denker | 600/17 |
| 6,110,100 A * | 8/2000 | Talpade | 600/37 |
| 6,123,724 A * | 9/2000 | Denker | 623/3.11 |
| 6,494,825 B1 * | 12/2002 | Talpade | 600/16 |
| 6,600,952 B1 | 7/2003 | Snell et al. | 607/31 |
| 2003/0083702 A1 | 5/2003 | Stadler et al. | 607/14 |
| 2003/0105496 A1 | 6/2003 | Yu et al. | 607/17 |
| 2004/0010180 A1 * | 1/2004 | Scorvo | 600/16 |
| 2005/0113635 A1 * | 5/2005 | Whayne et al. | 600/37 |
| 2005/0148814 A1 * | 7/2005 | Fischi et al. | 600/37 |
| 2006/0041183 A1 * | 2/2006 | Massen et al. | 600/16 |
| 2006/0155160 A1 * | 7/2006 | Melvin et al. | 600/16 |

FOREIGN PATENT DOCUMENTS

| | | |
|---|---|---|
| WO | WO03/37177 A2 | 8/2000 |
| WO | WO03/37177 A3 | 8/2000 |

* cited by examiner

*Primary Examiner*—Kristen D. Mullen
*Assistant Examiner*—Eugene T Wu

(57) ABSTRACT

An elastic framework configured to be positioned around a portion of the heart has a plurality of first regions and a plurality of second regions positioned relative to the first regions. The framework allows for the positioning of the first regions and second regions adjacent the outer surface of the heart and is structured so that the regions experience different movement effects in response to expansion and contraction of the heart. A sensor network having at least one motion sensor system associated with one of the first regions and second regions is associated with the framework. The motion sensor system outputs data responsive to the relative movement effects of the first and second regions. A communications system in communication with the sensor network provides for the transmission of motion data to a location remote from the framework.

13 Claims, 7 Drawing Sheets

US 7,338,436 B1

IMPLANTABLE CARDIAC PHYSICAL MOTION MAPPING DEVICE

FIELD OF THE INVENTION

The invention relates generally to cardiac rhythm management devices and, more particularly, to implantable cardiac physical motion monitoring devices.

DESCRIPTION OF RELATED ART

Cardiac rhythm management (CRM) devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac devices may also include the combined functionalities of a pacemaker and a defibrillator.

Implantable cardiac stimulation devices sense cardiac activity for monitoring the cardiac condition of the patient in which the device is implanted. By sensing the electrical cardiac activity of the patient, the device is able to provide cardiac stimulation therapy when it is required. It has been recognized that other indicators of heart function, such as mechanical heart function, would be of great value in managing cardiac rhythm. For example, in a cardiac resynchronization therapy (CRT) system, direct mechanical measurement of ventricular wall synchronization would allow the mechanical effects of manipulating cardiac electrical activity to be observed.

It has thus been recognized that knowledge of mechanical activity of the heart may provide significant insight into the condition of the heart as well as a means for optimizing various CRM therapies including, not only CRT, but also anti-arrhythmia, atrial-ventricular (AV) timing and others.

SUMMARY

Briefly, and in general terms, what are described herein are implantable cardiac motion monitoring devices, cardiac rhythm management devices employing implantable motion monitoring devices and related methods of measuring and monitoring cardiac motion. In one aspect, an implantable cardiac motion monitoring device is described that includes an elastic framework having a plurality of first regions and a plurality of second regions positioned relative to the first regions. The framework is structured so that the first regions and second regions experience different movement effects when subjected to a force. The device further includes a motion sensor system associated with at least one of the first regions and second regions that outputs data responsive to the relative movement effects of the first and second regions.

In another aspect, an implantable device is described for measuring movement at an outer surface of a heart. The device includes an elastic framework having a plurality of first regions and a plurality of second regions positioned relative to the first regions. The framework allows for the positioning the first regions and second regions adjacent the outer surface of the heart and is structured so that the regions experience different movement effects in response to expansion and contraction of the heart. The device also includes a sensor network having at least one motion sensor system associated with one of the first regions and second regions.

The motion sensor system outputs data responsive to the relative movement effects of the first and second regions. The device further includes a communications system in communication with the sensor network. The communication system allows for the transmission of motion data to a location remote from the framework.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
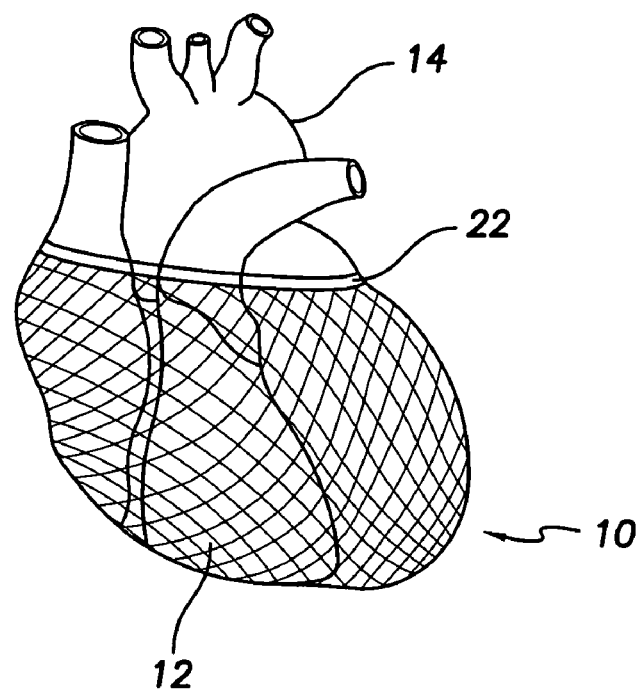
FIG. 1 is an illustration of one embodiment of an implantable motion monitoring device placed around a heart.
Figure 2:
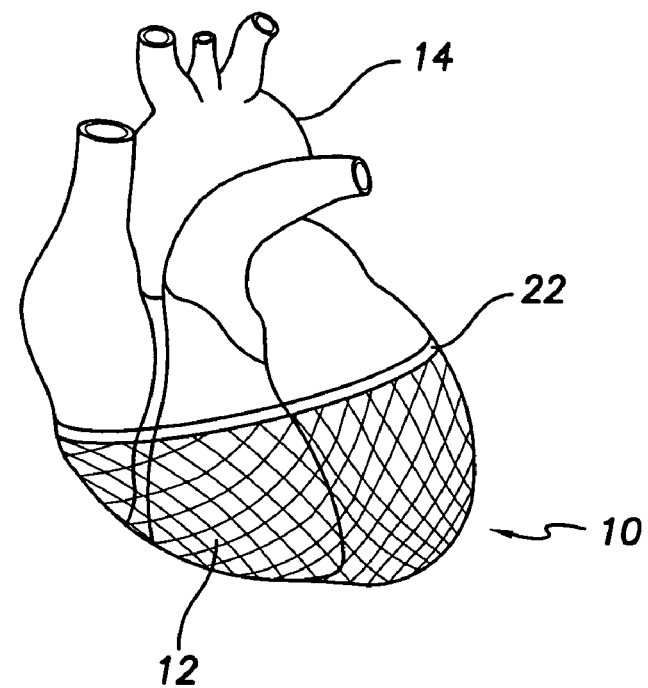
FIG. 2 is an illustration of another embodiment of an implantable motion monitoring device surrounding a portion of a heart.

With reference to FIGS. 1 and 2, an implantable motion mapping device 10, in accordance with the invention, includes an elastic framework 12 configured to be placed around a body organ 14, e.g. a heart. In one configuration (FIG. 1) the framework 12 may be described as an elastic web that surrounds most of the heart 14. In an alternative configuration (FIG. 2), the framework 12 resembles a sock or pouch that surrounds a portion of the heart 14. In either configuration, the elastic framework 12 is open at one end or side to allow for placement on the heart 14.

Figure 3:
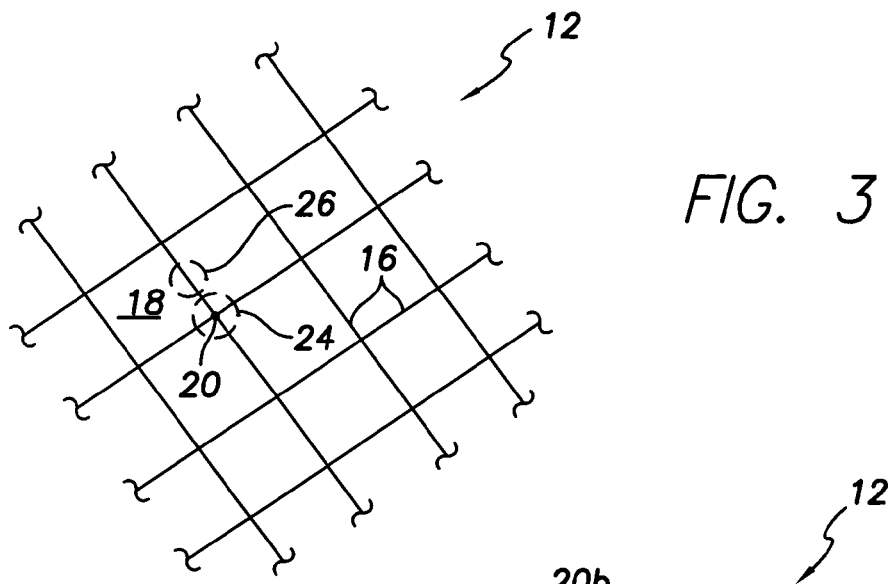
FIG. 3 is an illustration of an exemplary configuration of an elastic framework forming an implantable motion monitoring device.
Figure 4:
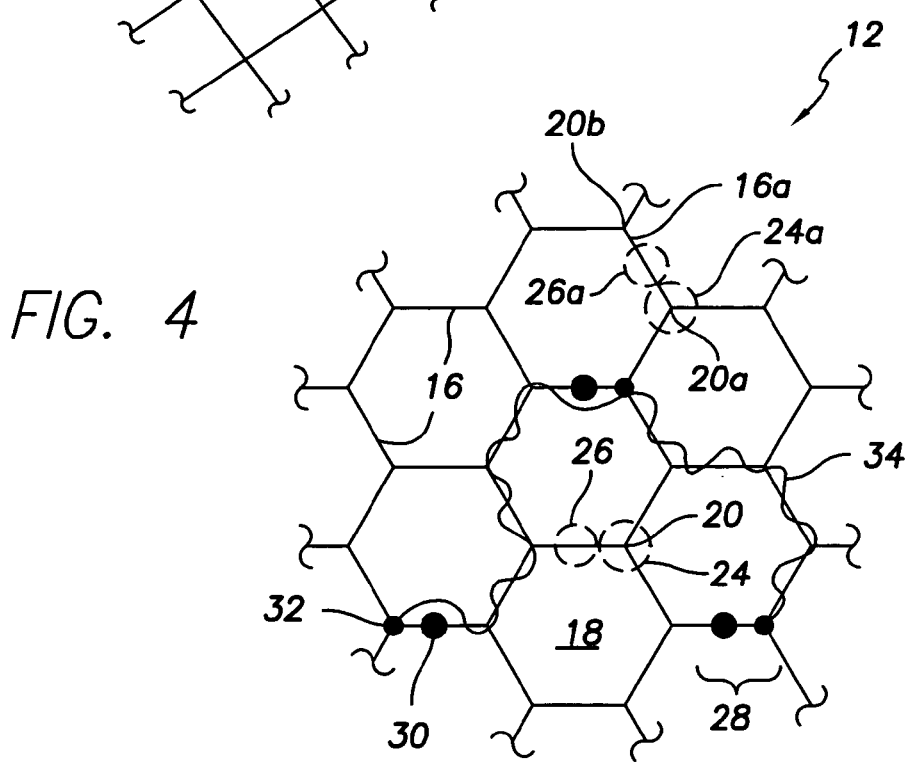
FIG. 4 is an illustration of another exemplary configuration of an elastic framework forming an implantable motion monitoring device.

With reference to FIGS. 3 and 4, the elastic framework 12 may be described as having elastic members 16 interconnected at their ends to form a generally geometric pattern defining openings 18. The openings 18 may have a generally polygonal shape, which as used herein in meant to encompass any opening bounded by three or more lines. Other shaped openings are also contemplated, such as circles and polygons with rounded corners.

The term "elastic members" is used herein as an aid in describing the structural features of the framework 12. The elastic members 16 are not necessarily individual piece parts physically connected together. To the contrary, for example, the framework 12 may be manufactured from a sheet of material, portions of which are removed by a laser to form the openings.

The connection points 20 of the elastic members 16 form the nexuses of the framework 12 and the corners of the polygonal openings 18. The elastic members 16 define the sides of the polygonal shape. The polygonal shape may be any one of numerous configurations, including a rectangle (FIG. 3) or a hexagon (FIG. 4). The framework 12 may also have a combination of polygonal shapes.

As shown in FIGS. 1 and 2, when applied to the heart 14, a framework 12 can be placed over or under the parietal pericardium. The framework 12 can be secured to the epicardium by a securing arrangement mounted at the base of the jacket. A suitable securing arrangement includes, for example, a circumferential attachment device 22, such as an elastic draw string or cord that closes the framework 12 around the heart. The circumferential attachment device 22 may also be a suture band, adhesive or shape memory element which passes around the circumference of the base of the framework. The ends of the attachment device 22 can be fastened together to secure the framework 12 in place. Alternatively, the base of the framework 12 can be reinforced for suturing the base of the jacket to the epicardium.

The framework 12 is made from an elastic biomedical material which can be applied to the surface of the heart. The biomedical material has an elastic nature that provides both adequate force to keep the framework 12 in place and sufficient flexibility to move with the expansion and contraction of the heart without impairing normal systolic function. Examples of suitable biomedical materials include perforate and non-perforate materials. Perforate materials include, for example, a mesh such as a polypropylene or polyester material. Non-perforate materials include, for example, silicone rubber or open-pore foam, such as silicone foam.

With reference to FIGS. 3 and 4, the arrangement and connection of the elastic members 16 provides a framework 12 which has regions of different elastic, stretching or movement characteristics. More specifically, the regions 24 of the framework 12 surrounding a nexus 20 are less susceptible to movement than the regions 26 of the framework removed from a nexus. For example, as shown in FIG. 4, the region 24a at or near the nexus 20a experiences less movement with respect to the cardiac wall than the region 26a midway along an elastic member 16a and between two nexuses 20a, 20b.

Figure 5:
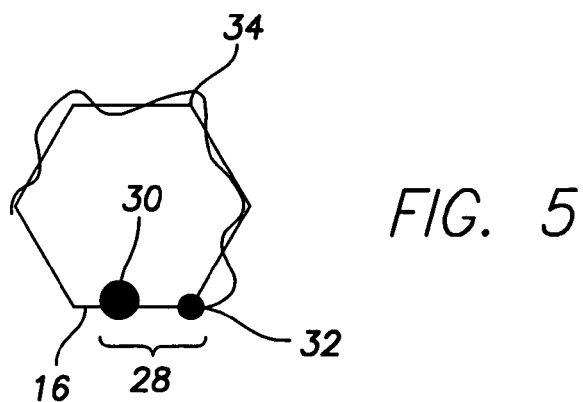
FIG. 5 is an illustration of a portion of the framework of FIG. 4 including a motion sensor system.

With reference to FIGS. 4 and 5, the framework 12 includes a number of motion sensor systems 28 which are preferably arranged around the framework. In one embodiment, the motion sensor systems 28 include a small permanent magnet 30 and an associated magnetic field sensor 32. Such magnetic sensor systems are commercially available from several manufacturers. Each of the magnet 30 and sensor 32 are mounted on the framework 12 surrounding the heart, such that both are adjacent the heart wall. One of the magnet 30 and sensor 32 is mounted at or near a nexus 20 while the other of the magnet and sensor is mounted about midway along an elastic member 16. In a preferred embodiment, the sensor 32 is mounted at the nexus 20 and the magnet 30 is mounted on the elastic member.

One or both of the magnet 30 and the magnetic sensor 32 may be placed within a small enclosure in order to insulate the heart wall from electrical current which may be carried by the sensor and contamination from the sensor and/or the magnet if either is made from a non-biocompatible material. These enclosures may be used to provide a means of attaching the sensor 32 and magnet 30 to the framework 12. Exemplary means of attaching enclosures to the framework include crimps, screws and adhesive.

As previously described, the framework 12 may be secured to the heart through an attachment device 22 or by suturing. In order to reduce movement of the motion mapping device 10 after placement on the heart, the framework 12 may be further secured to the heart at various points remote from the attachment device 22. For example, various connection points 20 of the framework 12 may be individually secured to the heart through a mechanical device, such as a screw, or through chemical adhesion. Alternatively, or in addition to securing the connection points 20, various of the motion sensor systems 28 attached to the framework 12, or components thereof (e.g., the magnet 30 or field sensor 32), may be secured to the heart.

As the heart expands and contracts, the magnet 30 and the sensor 32 move along with the immediately adjacent cardiac wall. Because one of the devices 30, 32 moves more than the other, the two devices tend to move either away from, or toward each other. This relative movement results in a relative change in the magnetic field created by the permanent magnet 30 as sensed by the magnetic field sensor 32. This change in magnetic field is proportional to the local expansion or contraction of the cardiac wall.

More specifically, assuming the sensor 32 is at a nexus 20 and the magnet 30 is on the elastic member 16, expansion of the heart tends to move the magnet away from the sensor, thereby reducing the magnetic field imposed on the sensor by the magnet. Conversely, contraction results in the magnet 30 moving closer to the sensor 32, thereby increasing the field. Thus the magnetic field strength would be directly representative of the local heart motion.

A framework 12 may include various numbers of sensor systems 28. For example, a framework 12 intended to be used in applications where only low detailed or "coarse" motion monitoring is needed may include approximately 8 sensor systems 28, whereas a framework to be used in applications where high detailed or "fine" motion monitoring is desired may include approximately 128 sensor systems. The number of sensor systems 28 on a framework 12 and their positioning relative to each other may be affected by the properties of the sensor system, particularly the sensitivity of the sensor 32. The sensitivity of the sensor 32, in turn, may be a function of the power applied to the sensor. Thus, the arrangement and density of sensor systems 28 on a framework 12 may be considered a function of sensitivity and power.

If the amount of power provided to a sensor 32 produces a highly sensitive sensor, the further the sensor's associated magnet 30 may be placed from it. However, at the same time, the magnets 30 of adjacent sensor systems 28 must be placed sufficiently far from the sensor 32 so that the sensor does not experience interference through the detection of adjacent magnet movement. Thus, high power application and high sensor sensitivity would tend to require the use of fewer sensor systems and thus would produce a coarse motion monitoring device 10. An exemplary coarse motion monitoring device may include approximately 8 sensors systems. At the other end of the spectrum, if the amount of power provided to a sensor 32 results in low sensor sensitivity, the closer the sensor's associated magnet 30 must be placed to it. The lower sensitivity allows for adjacent magnets 30 to be placed closer to the sensor 32 without interference. Thus, low power application and low sensor sensitivity would tend to allow the use of more sensor systems 28 and thus would produce a "fine" motion monitoring device 10. An exemplary fine motion monitoring device may include approximately 128 sensors systems.

While the motion sensors just described are magnetic based sensors, other types of motion sensors, such as strain gauges, accelerometers, ultrasound transducers and electro-active polymer material sensors may be used. These devices may be enclosed and attached to framework 12 in a manner similar to that described with respect to the magnetic sensor systems 28. Strain gages, accelerometers and electro-active polymer sensors may be positioned on the framework 12 either on or near a nexus 20 or on an elastic member 20. Ultrasound transducer system which includes an ultrasound transducer and an ultrasound sensor may be positioned on a framework in the same manner as the described magnetic sensor system, with the sensor portion on or near a nexus and the transducer portion in the region between two nexuses. Other types of sensors, unrelated to motion, may also be included in the motion monitoring device, such as temperature sensors.

With respect to the electro-active polymer sensors, the polymer materials that form these sensors are elastic and thus may be formed as part of the framework 12 instead of as components separate from the framework, as previously described. These electro-active polymer materials output electrical signals, e.g., voltage signals, when they experience a change in strain. One example of a possible electro-active polymer material that may be used as a sensor is silicone dielectric elastomers. These elastomers are soft, flexible and biocompatible.

The preferred type of sensor system 28 may varying depending on the intended application of the motion monitoring device 10. For example, if the condition to be monitored involves reduced mechanical motion of the heart wall that is hard to detect, an accelerometer, which uses acceleration measurements to calculate movement, may be preferred over a magnet sensor system which uses velocity measurements to calculate movement. An example of such a condition is an enlarged heart. If the condition to be monitored involves velocity related activity, such as a slow down in heart rate, then magnet sensor systems would be preferable. For a condition involving long term trend monitoring, such as the effects of ischemia on heart function, either one or a combination of magnetic sensor systems and accelerometers may be used. In these cases, the measurements detected by the sensors are used to determine a normal measurement against which future measurements are compared. Deviations from the normal measurement may be indicative of abnormal heart movement such as a slow down in heart rate.

As described further below, it may be desirable to know which motion sensor systems 28 are associated with particular regions of the heart. To allow for this, x-ray markers (not shown) may be placed on the framework 12 to determine the structural position on the heart. Thus, specific and identifiable motion sensor systems 28 could be associated with any regions of the heart including the left side of the heart, the right side of the heart, the ventricles including one or both of the left ventricle and the right ventricle, the atria including one or both of the left atrium and the right atrium, etc. Once the motion sensor systems 28 are positioned and associated with a region of the heart, the motion mapping device 10 is secured to the heart through the attachment device 22 of the framework 12. In this case, in order to maintain the association between particular motion sensor systems 28 and their associated heart region, elements of the motion mapping device 10 closer to the heart regions, such as the connection points 20 of the framework 12 or the motion monitoring systems 28 themselves, are preferably secured to the heart through mechanical or chemical means, as previously described.

Using the motion monitoring device 10 and a sensor switch (described below), motion activity from the heart may be monitored in any of several ways. In its simplest form, each motion sensor system 28 in a motion monitoring device 10 has a dedicated lead connection to the sensor switch and data is collected from each sensor system, one at a time. Such a configuration is feasible for a limited number of motion sensor systems 28. For a motion monitoring device with a large number of motion sensor systems 28, the sensor systems may be grouped together, such as through a daisy chain topology, and connected to the sensor switch through one or more leads. In these cases, data from all motion sensors is collected in sequence with each piece of data in the sequence corresponding to one of the sensor systems in the group. A multiplexer function provided, for example by a microcontroller, partitions the stream of cardiac motion data into its sequential parts and associates each part with a particular motion sensor system 28. Knowing the sequential position of a particular motion sensor in its group, allows for the selective monitoring of particular motion sensors.

In another arrangement, the sensor systems may be arranged within the motion monitoring device in groups, for example, by a daisy chain topology, such that all motion sensors associated with a particular region of the heart are chained together in a single group. Thus, one group may be associated with the right atrium, one with the left atrium, one with the right ventricle and one with the left ventricle. When a particular group of motion sensors is being monitored, the data collected is a sequence of data, with each piece of data in the sequence corresponding to one of the motion sensors in the group.

With continued reference to FIGS. 4 and 5, the motion sensor systems 28 within the framework 12 are preferably electrically interconnected to allow for the output of sensor data through a single output line. This interconnection may be provided by lightweight insulated cable wire conductors 34 woven around the elastic members 16. The conductors 34 are woven loose enough to allow for the expansion and contraction of the heart and framework. As previously described, the interconnection of the motion sensor systems 28 and cables 34 may be arranged in a "daisy-chain" loop (FIG. 4). Alternatively, a "star" (not shown) or other interconnection topology may be used.

The interconnected motion sensor systems 28 form all or a portion of a sensor network. As described further below, a sensor network may also include other sensing devices, such as temperature sensors and accelerometers. The sensor network may also include motion sensor circuitry and other circuitry associated with the other sensors included in the network.

Figure 6:
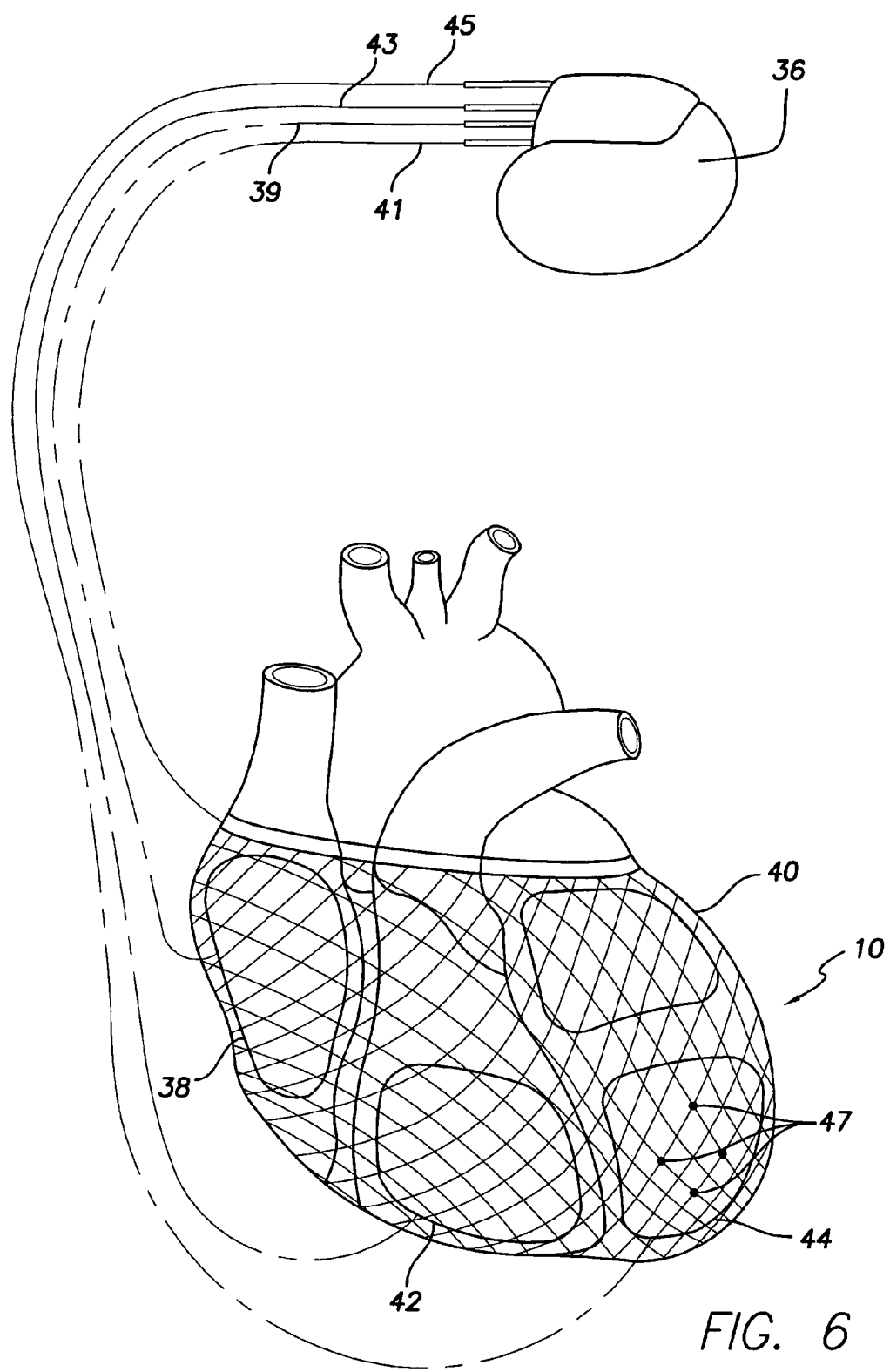
FIG. 6 is an illustration of an implantable cardiac motion monitoring device including a motion monitoring device placed on a heart and in communication with an electronic device.

With reference to FIG. 6, the implantable motion monitoring device 10 in conjunction with an implantable electronic device 36 form an implantable cardiac motion monitoring device. The electronic device 36 is in communication with the motion monitoring device 10 through one or more leads. In one embodiment, the motion monitoring device 10 is partitioned into four motion monitoring networks or regions 38, 40, 42, 44, including a right atrium region 38, left atrium region 40, right ventricle region 42 and left ventricle region 44. Each region has a lead 39, 41, 43, 45 in communication with the electronic device 36. Although the motion monitoring device 10 is described herein as having four regions, the device may be configured to include greater or fewer regions.

Figure 7:
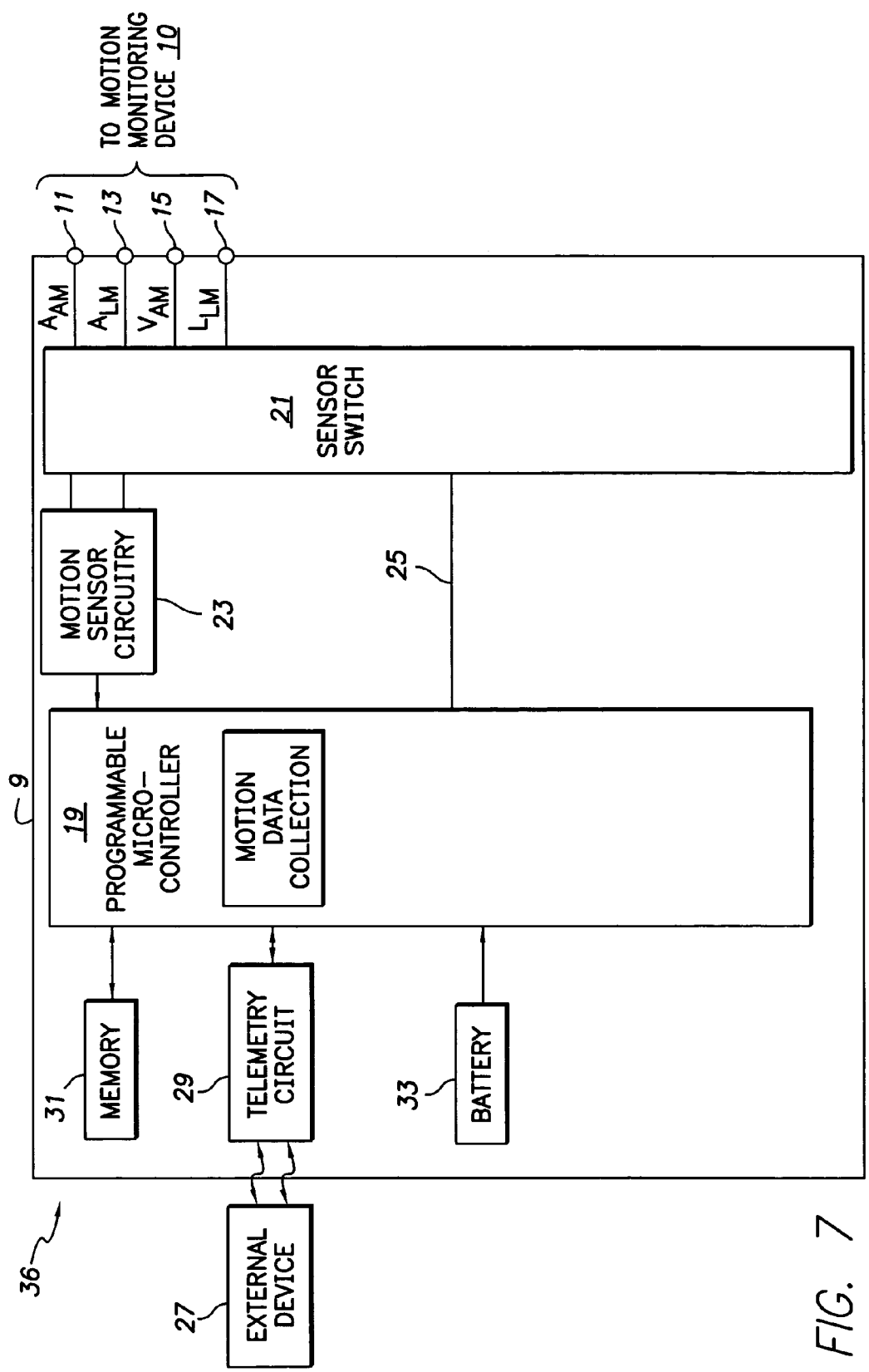
FIG. 7 is a functional block diagram of the implantable cardiac motion monitoring device of FIG. 6.

With reference to FIG. 7, a simplified block diagram of the implantable electronic device 36 includes a housing 9 having a connector (not shown) with a plurality of terminals 11, 13, 15, 17. These terminals include a right atrial terminal 11 adapted for connection to the right atrial region of the motion monitoring device, a left atrial terminal 13 adapted for connection to the left atrial region of the motion monitoring device, a right ventricle terminal 15 adapted for connection to the right ventricle region of the motion monitoring device and a left ventricle terminal 17 adapted for connection to the left ventricle region of the motion monitoring device.

The electronics device 36 includes a programmable microcontroller 19 that processes the various motion data received from the motion monitoring device 10. The microcontroller 19 includes a microprocessor, or equivalent control circuitry, designed specifically for processing the motion data and may further include RAM or ROM memory, logic and timing circuitry, state machine circuitry, and I/O circuitry. Typically, the microcontroller 19 includes the ability to process or monitor input signals (data) as controlled by a program code stored in a designated block of memory.

The microcontroller 19 may be programmed to include one or more motion data collection processes that allow it to generate a collection of motion data. This motion data may be in a form that correlates each of a number of sets of particular motion data with a particular time. The motion data may also be in a form that presents a sequence of sets of motion data having a time-between-sequence element associated with it. The microcontroller 19 may also form the motion data on a sensor by sensor basis. In this respect, the motion sensor systems 28 may have a local memory device that allows them to store sensed data for subsequent access by the microcontroller 19.

The microcontroller 19 may also correlate particular motion data with particular regions of the heart. For example, during cardiac resynchronization therapy (CRT), relative movement of the left ventricle and the right ventricle may be monitored to determine if the ventricle contractions are asynchronous and if resynchronization is necessary.

Data collected by the processor may be used to perform long term tracking of wall motion at the various sensors and various regions of the heart. For example, a patient with congestive heart failure (CHF) may experience ventricular dilation. As the ventricles dilate, the sensor systems in the ventricular regions will experience less movement. This reduction in movement will be reflected in the motion data. Monitoring changes in the motion data associated with the ventricular region over a period of time could be used to track the progression of congestive heart failure. Similar data may be collected to monitor atrial fibrillation burden and to detect small deformations of the heart due to posture (gravity).

In a basic configuration, the implantable electronic device 36 includes a sensor switch 21 through which one or more of the motion data received at the terminals 11, 13, 15, 17 is passed to motion sensor circuitry 23. The switch 21 operates under control of the microcontroller 19 through control line 25 and may be switched to collect motion data from the various regions sequentially (in series), or simultaneously (in parallel). The motion data received at the terminals is indicative of the relative motion of the components of each of the motion sensor systems 28 (FIG. 5) associated with a particular region 38, 40, 42, 44 (FIG. 6). The motion sensor circuitry 38 may include, for example, amplifiers to amplify the signals received from the motion sensor systems 28 to improve the signal-to-noise ratio and provide a signal level and shape acceptable for further processing by the microprocessor 19.

The microcontroller 19 processes the motion data received from the motion monitoring circuitry 23 and outputs it to an external device 27 through a communications system 29. In one configuration, the communications system 29 may include telemetry circuitry that communicates with the external device 27 upon receipt of an initiation command from the external device. Such telemetry circuitry and communications systems are known in the art and are described, for example, in U.S. Pat. No. 6,600,952, "Secure Telemetry System and Method for an Implantable Cardiac Stimulation Device," the disclosure of which is hereby incorporated by reference.

Communication with the external device 27 may be in real-time. Alternatively, communication with the external device 27 may be periodic, in which case, the implantable electronic device 36 further includes a memory device 31 for storing the processed data. In another configuration, data from the motion sensor circuitry 23 may be output directly to the communications system 29 and transmitted to the external device 27 for further processing. In yet another configuration, sensed data may be stored locally at the motion sensor systems 28 for subsequent transmission to the external device 27.

Motion data allows for monitoring of cardiac physical motion by mapping of exterior wall motion at a plurality of points on the heart. This wall motion data may be input to an external graphics display processor for integration with a three dimensional heart model to visualize the cardiac mechanical activity. Because the data may be accessed via telemetry it could be monitored in a catheter lab, clinic, at home, or other remote location using the same type of equipment that is used for monitoring IEGM telemetry from pacemakers and defibrillators.

With respect to a power source and modes of operation, the implantable electronic device 36 may take several forms. In one configuration, the implantable electronic device 36 includes a permanent battery power source 33 that continuously powers the motion monitoring device, the motion sensor circuitry 23 and the microcontroller 19 to allow for continuous collection of motion data from the motion monitoring device 10. This data is stored in a memory device. The communication system 29 is periodically powered up through interrogation from an external device 27 and the stored data is transmitted to the external device. In a configuration similar to that just described, the implantable electronic device 36 includes a rechargeable power source 33.

In another configuration, the implantable electronic device 36 does not include a power source. Instead, an external power source periodically powers the motion monitoring device 10, the motion sensor circuitry 23 and the microprocessor 19 to allow for collection of motion data from the motion monitoring device 10. The collected data is either stored in memory 31 until the implantable electrical circuitry is interrogated or, if interrogation is concurrent with power up, the motion data is transmitted in real time.

Power application to the motion monitoring device 10 may also be dependent on the monitoring application of the device. For long term monitoring, the microprocessor 19 may be programmed to include a multiplex power application function that periodically applies power to one sensor system 28 or a group of sensor systems. For example, one sensor system 28 may be powered per heart beat. Thus, for a fifty sensor system motion monitoring device 10, one sensor measurement would be obtained from each sensor system every fifty heart beats. A set of average measurements, per sensor system 28 or sensor system group, could be calculated based on a collection of measurements over a period of time, e.g., one hour. These average measurements could, in turn, be monitored over the course of a longer time period, e.g., 24 hours, to detect trends in the way the heart is operating. Powering the motion monitoring device 10 in this manner conserves power.

In other situations it may be necessary to monitor all or a large portion of the sensors in the motion monitoring device 10 on a more continuous basis in order to provide for a quick detection and response. For example, erratic pulsating of the heart is indicative of atrial fibrillation. Because this pulsating of the heart may occur in one or more of several areas of the heart, the microprocessor 19 may be programmed to apply power to all sensor systems 28 or a large group of sensor systems on a more frequent, almost continuous basis. For example, all or one-half of the sensor systems 28 may be powered per heart beat.

Figure 8:
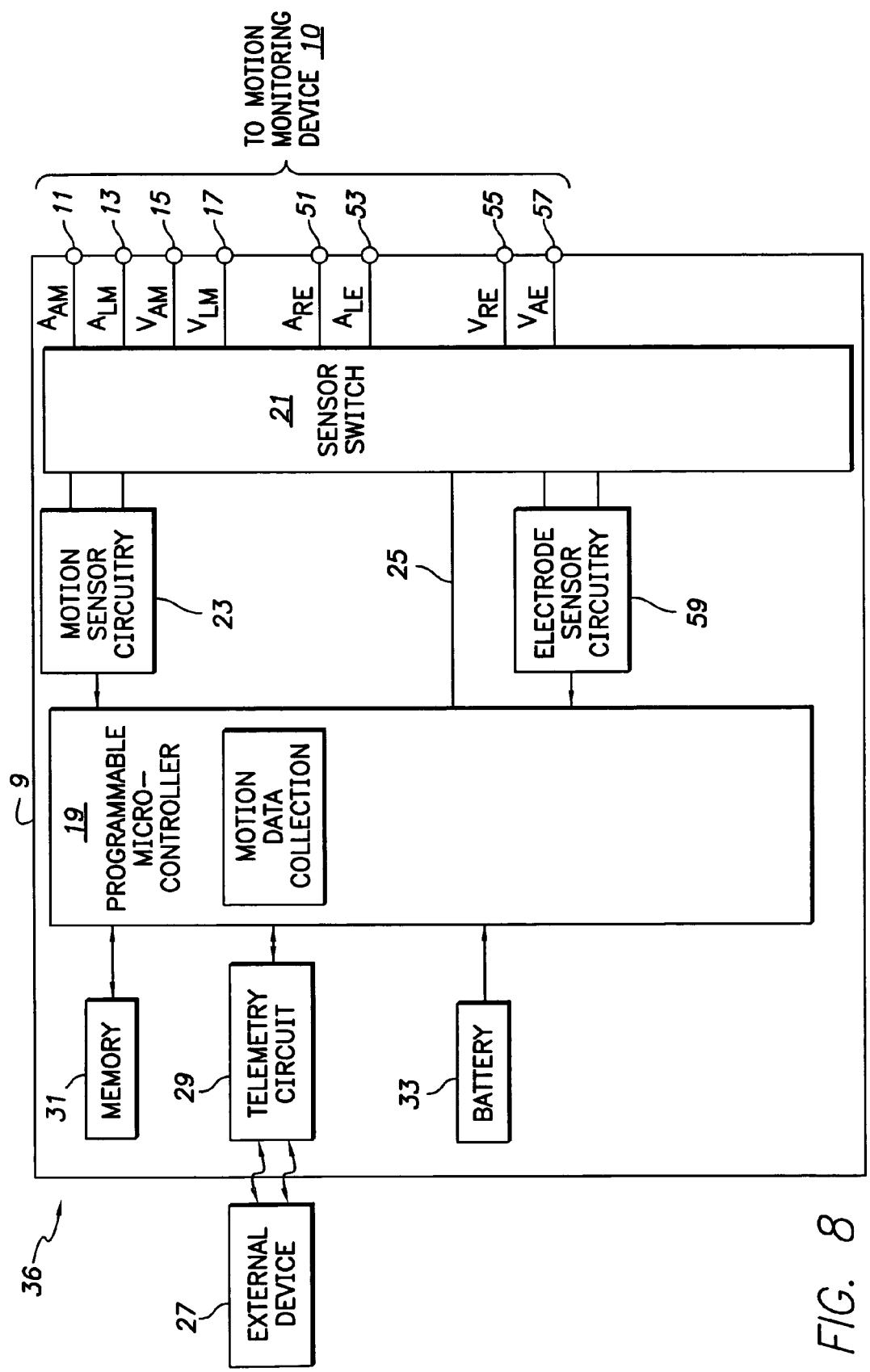
FIG. 8 is a functional block diagram of the implantable cardiac motion monitoring device having electrical sensing capabilities.

With reference to FIG. 8, in other configurations, the implantable cardiac motion monitoring device may include an electrode system having electrical sensing capabilities. For example, the motion monitoring device 10 (FIG. 6) may include one or more arrays of sensing electrodes 47 in contact with the exterior of the heart. These electrodes may be used to record local electrical activity of the heart, in the form of surface electrocardiograms (ECG). The sensing electrodes may be collocated with the motion sensor systems 28 (FIG. 5) or at separate locations.

In such a configuration, the implantable electronic device 36 includes additional connector terminals 51, 53, 55, 57 adapted to be connected to the electrodes on the motion monitoring device 10. These terminals include a right atrial terminal 51 adapted for connection to the right atrial sensing electrodes, a left atrial terminal 53 adapted for connection to the left atrial sensing electrodes, a right ventricle terminal 55 adapted for connection to the right ventricle sensing electrodes and a left ventricle terminal 57 adapted for connection to the left ventricle sensing electrodes.

The electronic device 36 also includes electrode sensor circuitry 59, which may include, for example, amplifiers to amplify the signals received from the electrodes to provide a signal level and shape acceptable for further processing by the microcontroller 19. In this configuration, the sensor switch 21 operates under control of the microcontroller 19 to pass one or more of the sensed signals to the electrode sensor circuitry 59.

A device having this configuration can simultaneously monitor cardiac wall motion and electrogram activity around the periphery of the heart. The ECG data provided by the array of electrodes may be used to map for ischemic regions and track progression; detect electro-mechanical disassociation (EMD); and/or detect electrical sequence of activation for comparison to mechanical activity. The later capability may be used in conjunction with a CRT device to provide for adjustment of CRT parameters.

Using the sensing electrodes and sensor switch 21, electrical activity from the heart may be monitored in any of several ways. In its most simple form, each sensing electrode has a dedicated lead connection to the sensor switch and data is collected from each sensing electrode, one at a time. In other forms, the sensing electrodes may be grouped together, such as through a daisy chain topology, and connected to the sensor switch through a single lead. In this case, data from all electrodes is collected in sequence with each piece of data in the sequence corresponding to one of the electrodes in the group. As with the previously described motion data, the microcontroller partitions the sequence of cardiac electrical data into parts and associates each part with a particular electrode. Knowing the sequential position of a particular electrode in its group, allows the microcontroller to selectively monitor particular electrodes.

In another arrangement, the sensing electrodes may be arranged within the motion monitoring device in groups, for example, by a daisy chain topology, such that all electrodes associated with a particular region of the heart are chained together in a single group. Thus, one group may be associated with the right atrium, one with the left atrium, one with the right ventricle and one with the left ventricle. When a particular group of electrodes is being monitored, the data collected is a sequence of cardiac electrical data, with each piece of data in the sequence corresponding to one of the electrodes in the group. As previously described with respect to the motion monitoring systems, the sensing electrodes may be secured to the heart to maintain their association with a particular heart region.

Figure 9:
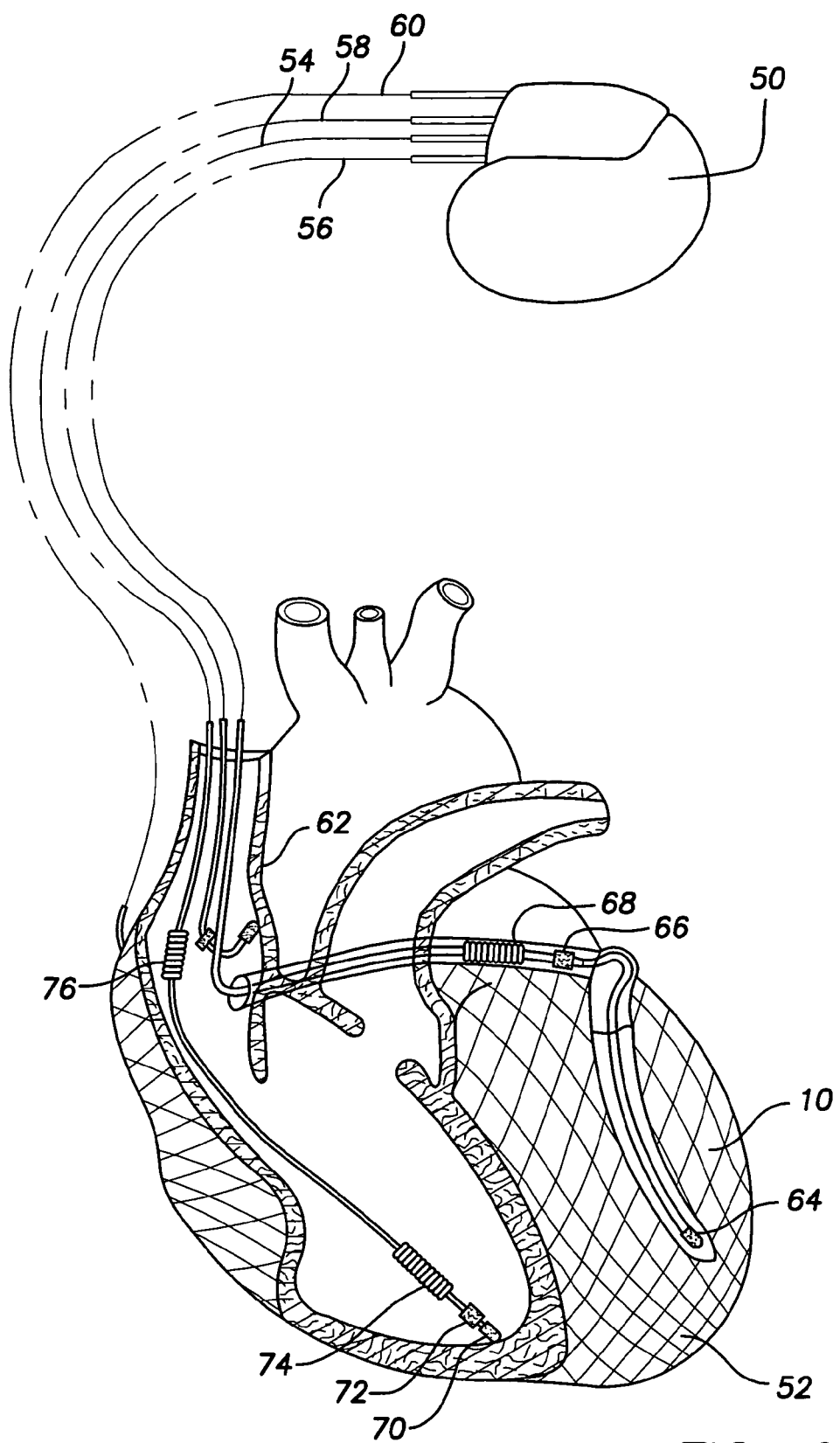
FIG. 9 is an illustration of an implantable cardiac stimulation and motion monitoring device including a motion monitoring device placed on a heart and electrode leads positioned within the heart, each in communication with an electronic device.

With reference to FIG. 9, in another configuration, the implantable motion monitoring device 10 is included as part of an implantable stimulation device 50 such as a pacemaker or defibrillator. The stimulation device 50 is in electrical communication with a patient's heart 52 by way of an electrode system including three leads 54, 56 and 58 suitable for delivering multi-chamber stimulation and shock therapy. The stimulation device is also in motion communication with the patient's heart through the motion monitoring device 10 and a motion sensor system lead 60.

To sense atrial cardiac signals and to provide right atrial chamber stimulation therapy, the stimulation device 50 is coupled to an implantable right atrial lead 54. The right atrial lead 54 has at least an atrial tip electrode 62, which typically is implanted in the patient's right atrial appendage.

To sense left atrial and ventricular cardiac signals and to provide left chamber pacing therapy, the stimulation device 50 is coupled to a "coronary sinus" lead 56 designed for placement in the "coronary sinus region" via the coronary sinus os for positioning a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. An exemplary coronary sinus lead 56 is designed to receive atrial and ventricular cardiac signals and to deliver left ventricular pacing therapy using at least a left ventricular tip electrode 64, left atrial pacing therapy using at least a left atrial ring electrode 66, and shocking therapy using at least a left atrial coil electrode 68.

The stimulation device 50 is also shown in electrical communication with the patient's heart 52 by way of an implantable right ventricular lead 58 having a right ventricular tip electrode 70, a right ventricular ring electrode 72, a right ventricular (RV) coil electrode 74, and an SVC (superior vena cava) coil electrode 76. Typically, the right ventricular lead 58 is transvenously inserted into the heart 52 so as to place the right ventricular tip electrode 70 in the right ventricular apex so that the RV coil electrode 74 will be positioned in the right ventricle and the SVC coil electrode 76 will be positioned in the superior vena cava. Accordingly, the right ventricular lead 58 is capable of receiving cardiac signals, and delivering stimulation in the form of pacing and shock therapy to the right ventricle.

Figure 10:
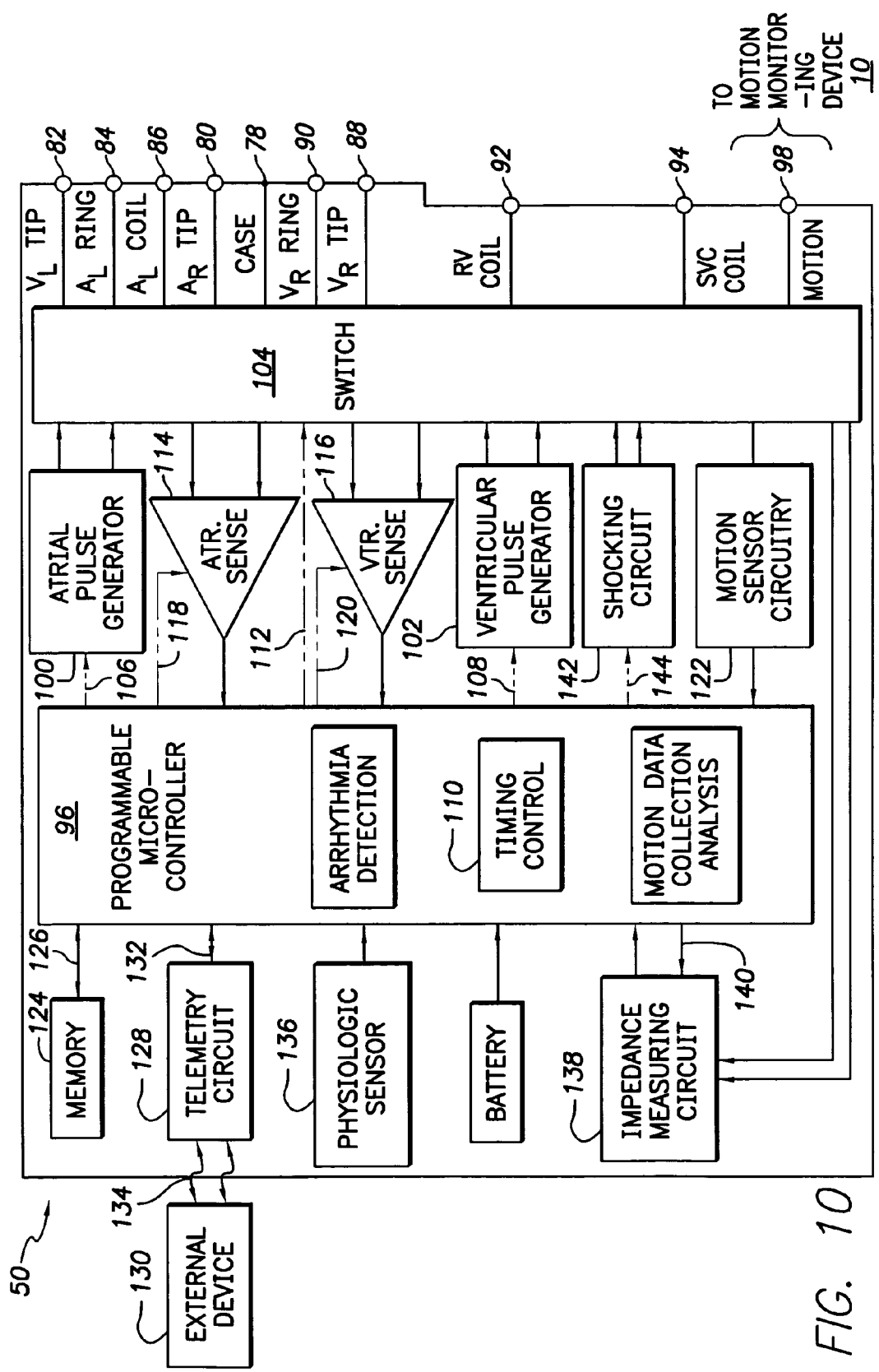
FIG. 10 is a functional block diagram of the implantable cardiac stimulation and motion monitoring device of FIG. 9.

With reference to FIG. 10, a simplified block diagram of the multi-chamber implantable stimulation device 50, capable of treating both fast and slow arrhythmias with stimulation therapy, including cardioversion, defibrillation, and pacing stimulation is shown. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 50 includes a housing 78 which is often referred to as "can", "case" or "case electrode", and which may be programmably selected to act as the return electrode for all "unipolar" modes. The housing 78 may further be used as a return electrode alone or in combination with one or more of the coil electrodes, 68, 74 and 76, for shocking purposes. The housing 78 further includes a connector (not shown) having a plurality of terminals 80, 82, 84, 86, 88, 90, 92, 94 and 98.

To achieve right atrial sensing and pacing, the connector includes at least a right atrial tip terminal ($A_R$ TIP) 80 adapted for connection to the atrial tip electrode 62. To achieve left chamber sensing, pacing and shocking, the connector includes at least a left ventricular tip terminal ($V_L$ TIP) 82, a left atrial ring terminal ($A_L$ RING) 84, and a left atrial shocking terminal ($A_L$ COIL) 86, which are adapted for connection to the left ventricular tip electrode 64, the left atrial tip electrode 66, and the left atrial coil electrode 68, respectively.

To support right chamber sensing, pacing and shocking, the connector further includes a right ventricular tip terminal ($V_R$ TIP) 88, a right ventricular ring terminal ($V_R$ RING) 90, a right ventricular shocking terminal ($R_V$ COIL) 92, and an SVC shocking terminal (SVC COIL) 94, which are adapted for connection to the right ventricular tip electrode 70, right ventricular ring electrode 72, the RV coil electrode 74, and the SVC coil electrode 76, respectively.

In accordance with the invention, to further support right and/or left chamber sensing, pacing or shocking, the connector further includes a motion sensor system terminal 98 (MOTION). The MOTION terminal 98 is adapted for connection to the motion monitoring device 10 through a lead 60.

The stimulation device 50 includes a programmable microcontroller 96 that controls the various modes of stimulation therapy. The microcontroller 96 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 96 includes the ability to process or monitor input signals (data) as controlled by a program code stored in a designated block of memory.

As shown in FIG. 10, an atrial pulse generator 100 and a ventricular pulse generator 102 generate pacing stimulation pulses for delivery by the right atrial lead 54, the right ventricular lead 58, and/or the coronary sinus lead 56 via an electrode configuration switch 104. As used herein, the shape of the stimulation pulses is not limited to an exact square or rectangular shape, but may assume any one of a plurality of shapes which is adequate for the delivery of an energy packet or stimulus.

In order to provide stimulation therapy in each of the four chambers of the heart, the atrial pulse generator 100 and the ventricular pulse generator 102 may include dedicated, independent pulse generators, multiplexed pulse generators, or shared pulse generators. The atrial pulse generator 100 and the ventricular pulse generator 102 are controlled by the microcontroller 96 via appropriate control signals 106 and 108, respectively, to trigger or inhibit the stimulation pulses.

The microcontroller 96 further includes timing control circuitry 110 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 104 includes a plurality of switches for connecting the desired electrodes to the appropriate I/O circuits, thereby providing complete electrode programmability. Accordingly, the switch 104, in response to a control signal 112 from the microcontroller 96, determines the polarity of the stimulation pulses (e.g., unipolar, bipolar, combipolar, etc.) by selectively closing the appropriate combination of switches (not shown) as is known in the art.

Atrial sensing circuits 114 and ventricular sensing circuits 116 may also be selectively coupled to the right atrial lead 54, coronary sinus lead 56, and the right ventricular lead 58, through the switch 104 for detecting the presence of cardiac activity in each of the four chambers of the heart. Accordingly, the atrial and ventricular sensing circuits 114, 116 may include dedicated sense amplifiers, multiplexed amplifiers, or shared amplifiers. The switch 104 determines the "sensing polarity" of the cardiac signal by selectively closing the appropriate switches, as is also known in the art. In this way, the clinician may program the sensing polarity independent of the stimulation polarity.

Each sensing circuit 114 and 116, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits 114 and 116 are connected to the microcontroller 96 which, in turn, are able to trigger or inhibit the atrial and ventricular pulse generators 100 and 102, respectively, in a demand fashion in response to the absence or presence of cardiac activity in the appropriate chambers of the heart. The sensing circuits 114 and 116, in turn, receive control signals over signal lines 118 and 120, from the microcontroller 96 for purposes of controlling the gain, threshold, polarization charge removal circuitry (not shown), and the timing of any blocking circuitry (not shown) coupled to the inputs of the sensing circuits, as is known in the art.

In accordance with the invention, the sensor switch 104 includes one or more switches for connecting the motion monitoring device 10 to motion monitoring circuitry 122. As previously mentioned, the motion sensor circuitry 122 may include, for example, amplifiers to amplify the signals received from the motion monitoring device 10 to improve the signal-to-noise ratio and provide a signal level and shape acceptable for further processing by the microprocessor 96. The motion data provided by the motion monitoring device 10 may be used in conjunction with, or in lieu of, the sensed cardiac electrical signals to trigger or inhibit the atrial and ventricular pulse generators 100, 102. Motion data received from the motion monitoring device 10 is input to the microprocessor 96. As previously described, certain regions of the motion monitoring device 10 may be associated with particular regions of the heart. In this case, the microprocessor 96 is able discriminate between ventricle motion data including left ventricle motion data and right ventricle data and atrial motion data including left atrium motion data and right atrium motion data.

Using these respective data, the microprocessor 96 compares the timing of contractions among the various parts of the heart. For example, during bi-ventricular stimulation or other cardiac resynchronization therapies, the motion data associated with the left ventricle may be compared with motion data associated with the right ventricle to determine if the physical contractions of the ventricles are synchronized. If appropriate synchronization is not detected, the interpulse delay, i.e., the time between left and right ventricular chamber pulse delivery, may be adjusted through appropriate control of the ventricular pulse generator 102 and the switch 104. Once adjusted, the physical contractions of the ventricles may be further monitored until uniform contraction is achieved. The foregoing process may also be used to monitor and synchronize the contractions of the atria.

As another example, during pacing stimulation, the motion data associated with the left and/or right atrium may be compared with motion data associated with the left and/or right ventricle to determine if the spacing between the physical contractions of the atria and the ventricles, i.e., the AV delay, is indicative of normal conduction. If an appropriate AV delay is not detected, the timing of the pulses output by ventricular pulse generator 102 and/or the atrial pulse generator 100 may be adjusted to optimize the AV delay.

For arrhythmia detection, the device 50 may utilizes the atrial and ventricular sensing circuits 114, 116 to sense cardiac signals to determine whether a rhythm is physiologic or pathologic. Alternatively, and in accordance with the invention, the device 50 may use the motion data sensed by the motion monitoring device 10 to determine whether a rhythm is physiologic or pathologic. The electrical sensed signals and the motion sensed signals may be used in conjunction with each other or independently to detect arrhythmia. As used herein "sensing" is reserved for the noting of an electrical signal or motion signal, and "detection" is the processing of these sensed signals and noting the presence of an arrhythmia.

Regarding the use of cardiac motion signals, the motion rates of various regions of the heart are monitored by the microprocessor and classified by the microprocessor by comparing them to predefined motion-rate zone limits (i.e., bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, antitachycardia pacing, cardioversion shocks or defibrillation shocks, collectively referred to as "tiered therapy"). With respect to the use of electrical sensed signals, the microprocessor classifies the signals by comparing predefined electrical-rate zone limits and various other characteristics to the timing intervals between sensed events (e.g. P-waves, R-waves, and depolarization signals associated with fibrillation which is sometimes referred to as "F-waves" or "Fib-waves").

The microcontroller 96 is further coupled to a memory 124 by a suitable data/address bus 126. The memory 124 stores the cardiac motion data and cardiac electrical data collected by the microcontroller 96. The memory 124 also stores the programmable operating parameters used by the microcontroller 96. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 52 within each respective tier of therapy.

Advantageously, the operating parameters of the stimulation device 50 may be non-invasively programmed into the memory 124 through a telemetry circuit 128 in telemetric communication with an external device 130, such as a programmer, transtelephonic transceiver, or a diagnostic system analyzer. The telemetry circuit 128 is activated by the microcontroller 96 by a control signal 132. The telemetry circuit 128 allows cardiac motion data, intracardiac electrograms and status information relating to the operation of the stimulation device 50 (as contained in the microcontroller 96 or memory 124) to be sent to the external device 130 through an established communication link 134.

The stimulation device 50 may further include a physiologic sensor 136, commonly referred to as a "rate-responsive" sensor because it is typically used to adjust pacing stimulation rate according to the exercise state of the patient. However, the physiological sensor 136 may further be used to detect changes in cardiac output, changes in the physiological condition of the heart, or diurnal changes in activity (e.g. detecting sleep and wake states). Accordingly, the microcontroller 96 responds by adjusting the various pacing parameters (such as rate, AV delay, V-V delay, etc.) at which the atrial and ventricular pulse generators, 100 and 102, generate stimulation pulses.

While the physiologic sensor 108 is shown as being included within the stimulation device 50, it is to be understood that the physiologic sensor 136 may also be external to the stimulation device 50, yet still be implanted within or carried by the patient. A common type of rate responsive sensor is an activity sensor, such as an accelerometer or a piezoelectric crystal, which is mounted within the housing 78 of the stimulation device 50. Other types of physiologic sensors are also known, for example, sensors that sense the oxygen content of blood, pressure, cardiac output, ejection fraction, stroke volume, end diastolic volume, end systolic volume, respiration rate and/or minute ventilation, pH of blood, ventricular gradient, etc. However, any sensor may be used which is capable of sensing a physiological parameter that corresponds to the exercise state of the patient.

As further shown in FIG. 10, the stimulation device 50 is shown as having an impedance measuring circuit 138 which is enabled by the microcontroller 96 by a control signal 140. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the heart valves, etc. The impedance measuring circuit 112 is advantageously coupled to the switch 74 so that any desired electrode may be used.

In the case where the stimulation device 10 is intended to operate as an implantable cardioverter/defibrillator (ICD)

device, it needs to detect the occurrence of an arrhythmia, and automatically apply an appropriate electrical shock therapy to the heart aimed at terminating the detected arrhythmia. To this end, the microcontroller 96 further controls a shocking circuit 142 by way of a control signal 144. The shocking circuit 142 generates shocking pulses of low (up to 0.5 Joules), moderate (0.5-10 Joules), or high (11 to 40 Joules) energy, as controlled by the microcontroller 96. Such shocking pulses are applied to the patient's heart 52 through at least two shocking electrodes, and as shown in this embodiment, selected from the left atrial coil electrode 68, the RV coil electrode 74, and/or the SVC coil electrode 76 (FIG. 7). As noted above, the housing 78 may act as an active electrode in combination with the RV electrode 74, or as part of a split electrical vector using the SVC coil electrode 76 or the left atrial coil electrode 68 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 96 is capable of controlling the synchronous or asynchronous delivery of the shocking pulses.

In another embodiment of the invention, the motion monitoring device includes an electrode system having one or more stimulation electrodes that function as pacing and/or defibrillation electrodes. The stimulation electrodes on the motion monitoring device replace the need for some or all of the implanted electrodes typically associated with cardiac stimulation devices. For example, instead of implanting the various atrial and ventricular electrodes 62, 64, 66, 68, 70, 72, 74 and 76, as shown in FIG. 9, electrodes are located on the motion monitoring device 10 such that when the device is positioned on the patient's heart, the stimulation electrodes are adjacent the cardiac wall at the locations where the implanted electrodes would have been. Such a device would be able to perform the functions previously described with respect to the embodiment shown in FIGS. 9 and 10.

It is possible that movement other than cardiac-wall movement will be sensed by the motion mapping device 10. For example, motion due to walking, running or constant vibration, such as may occur when riding on a train, will be sensed by the motion sensor systems 28. Sensor system 28 data resulting from such non-cardiac wall movement, hereafter referred to as "noise," may effect system operation and should be taken into accounted. Accordingly, each of the previously described systems are preferably designed, most likely through microprocessor programs and algorithms, to account for the effects of noise.

In one possible configuration, the microprocessor may include algorithms that analyze the sensed motion data and characterize the sensed motion as either cardiac-wall motion data or non-cardiac wall motion data. For example, motion due to walking will have signal levels and patterns different from motion due to heart movement. If the processor recognizes the motion as walking, it may discard the data. As another example, motion due to constant vibration will have average signal levels for a certain period of time that are inconsistent with signal levels associated with any heart rhythm, either normal or arrhythmic. This motion data may also be discarded by the system.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An implantable device for measuring movement at an outer surface of a heart, said device comprising:
   an elastic framework having a plurality of first regions and a plurality of second regions positioned relative to the first regions, the first regions and second regions positioned adjacent the outer surface and experiencing different movement effects in response to expansion and contraction of the heart;
   a sensor network comprising at least one motion sensor system including a magnetic sensor associated with the at least one first region and a magnet associated with the at least one second region, the sensor network outputting data responsive to the relative movement effects of the first and second regions; and
   a communications system in communication with the sensor network.

2. The device of claim 1 wherein the sensor network comprises a plurality of motion sensor systems each having a magnetic sensor associated with one of the first regions and a magnet associated with one of the second regions and a cable system interconnecting the motion sensor systems to each other and the communications system.

3. The device of claim 2 wherein the communications system receives sensor data from the sensor network and comprises a telemetry circuit that transmits the motion data to a location remote from the device.

4. An implantable cardiac motion monitoring device comprising:
   an elastic framework having a plurality of first regions and a plurality of second regions positioned relative to the first regions, the first regions and second regions experiencing different movement effects when subjected to a force; and
   a motion sensor system including a magnetic sensor associated with the at least one first region and a magnet associated with the at least one second region, the motion sensor system outputting data responsive to the relative movement effects of the first and second regions.

5. The device of claim 1 wherein the elastic framework comprises a plurality of elastic members interconnected to form a plurality of nexuses and a plurality of openings.

6. The device of claim 5 wherein the plurality of openings have a generally polygonal shape including corners and sides.

7. The device of claim 5 wherein at least one of the nexuses forms one of the first region and second region and a portion of at least one of the elastic members remote from the nexuses forms the other of the first region and second region.

8. The device of claim 1 wherein the motion monitoring system is formed as part of the elastic framework.

9. The device of claim 1 further comprising at least one temperature sensor associated with the elastic framework.

10. The device of claim 1 further comprising an attachment device for securing the motion monitoring device to a biological site.

11. An implantable cardiac motion monitoring device comprising:

an elastic framework having a plurality of nexuses defined by a plurality of interconnected elastic members, the framework having a plurality of first regions, each including a nexus, and a plurality of second regions, each including a portion of an elastic member remote from a first region, the first regions being less susceptible to movement than the second regions; and a motion sensor system having a first element associated with one of the first regions and a second element, separate from the first element, and associated with one of the second regions, the first element and the second element functioning together to output data responsive to the relative movement of the first element and the second element.

12. The device of claim 11 further comprising an electrode for sensing electrical activity, the electrode associated with one of the first regions.

13. The device of claim 11 wherein the first part comprises one of a magnet and a magnetic sensor and the second part comprises the other of a magnet and a magnetic sensor.

* * * * *